United States Patent [19]

Berger et al.

[11] Patent Number: 5,998,472
[45] Date of Patent: Dec. 7, 1999

[54] MIXED CYANOACRYLATE ESTER COMPOSITIONS

[75] Inventors: Thomas Jay Berger; Carlos Roberto Morales, both of Colorado Springs, Colo.; Richard J. Greff, St. Pete Beach, Fla.; Ian N. Askill, Colorado Springs, Colo.

[73] Assignee: MedLogic Global Corporation, Colorado Springs, Colo.

[21] Appl. No.: 09/169,640

[22] Filed: Oct. 9, 1998

Related U.S. Application Data

[63] Continuation-in-part of application No. 09/080,503, May 18, 1998, which is a continuation of application No. 08/947,792, Oct. 9, 1997, Pat. No. 5,753,699.

[51] Int. Cl.[6] .................. A61K 31/275; C07C 255/07

[52] U.S. Cl. .............................................. 514/527; 558/443
[58] Field of Search ............................... 558/443; 514/527

[56] References Cited

U.S. PATENT DOCUMENTS

| | | | |
|---|---|---|---|
| 5,480,935 | 1/1996 | Greff et al. | 524/776 |
| 5,753,699 | 5/1998 | Greff et al. | 514/527 |

*Primary Examiner*—Johann Richter
*Assistant Examiner*—Ebenezer Sackey
*Attorney, Agent, or Firm*—Burns Doane Swecker & Mathis, LLP

[57] ABSTRACT

Disclosed are mixed alkyl cyanoacrylate compositions which are specifically formulated for topical application onto intact or broken human skin, preferably without the addition of a plasticizing agent to the composition.

21 Claims, No Drawings

MIXED CYANOACRYLATE ESTER COMPOSITIONS

CROSS-REFERENCE TO RELATED APPLICATIONS

This application is a continuation-in-part of U.S. patent application Ser. No. 09/080,503, filed May 18, 1998 which, in turn, is a continuation of U.S. patent application Ser. No. 08/947,792 filed on Oct. 9, 1997, now U.S. Pat. No. 5,753,699 which issued on May 19, 1998 both of which are incorporated herein by reference in their entirety.

BACKGROUND OF THE INVENTION

1. Field of the Invention

This invention is directed to mixed alkyl cyanoacrylate compositions which are specifically formulated for topical application onto intact or broken human skin, preferably without the addition of a plasticizing agent to the composition.

2. References

The following publications, patent applications and patents are cited in this application as superscript numbers:

[1] Rabinowitz, et al., *Method of Surgically Bonding Tissue Together*, U.S. Pat. No. 3,527,224, issued Sep. 8, 1970

[2] Hawkins, et al., *Surgical Adhesive Compositions*, U.S. Pat. No. 3,591,676, issued Jul. 6, 1971

[3] Halpern, et al., *Adhesive for Living Tissue*, U.S. Pat. No. 3,667,472, issued Jun. 6, 1972

[4] Kronenthal, et al., *Surgical Adhesives*, U.S. Pat. No. 3,995,641, issued Dec. 7, 1976

[5] Davydov, et al., *Medical Adhesive*, U.S. Pat. No. 4,035,334, issued Jul. 12, 1977

[6] Waniczek, et al., *Stabilized Cyanoacrylate Adhesives Containing Bis-Trialkylsilyl Esters of Sulfuric Acid*, U.S. Pat. No. 4,650,826, issued Mar. 17, 1987

[7] Barley, *Methods of Retarding Blister Formation by Use of Cyanoacrylate Adhesives*, U.S. Pat. No. 5,306,490 issued Apr. 26, 1994

[8] Barley, et al., *Methods to Prevent Irritation Arising from Casts and Prosthesis*, U.S. Pat. No. 5,653,769 issued Aug. 5, 1997

[9] Tighe, et al., *Use of Cyanoacrylate Adhesives for Providing a Protective Barrier Film for the Skin*, U.S. Pat. No. 5,580,565 issued Dec. 3, 1996

[10] Askill, et al., *Methods for Draping Surgical Incision Sites*, U.S. Pat. No. 5,730,994 issued Mar. 24, 1998

[11] Greff, et al., *Cyanoacrylate Adhesive Compositions*, U.S. Pat. No. 5,480,935 issued Jan. 2, 1996

All of the above publications, patent applications and patents are herein incorporated by reference in their entirety to the same extent as if each individual publication, patent application or patent was specifically and individually indicated to be incorporated by reference in its entirety.

3. State of the Art

Cyanoacrylate esters are well known in the art and can be represented by formula I:

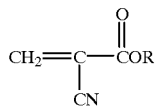

wherein R is an alkyl group or other suitable substituent forming the ester component of the molecule. Such cyanoacrylates are disclosed, for example, in U.S. Pat. Nos. 3,527,224; 3,591,676; 3,667,472; 3,995,641; 4,035,334; and 4,650,826.[1-6] Typically, when applied onto living tissue, the R substituent is most often lower alkyl (e.g., $C_1$ to $C_8$) and the corresponding alkyl cyanoacrylate esters are liquids at room temperature.

Heretofore disclosed uses for topical application of polymerizable cyanoacrylate compositions comprising lower alkyl cyanoacrylate esters to mammalian skin include application onto intact skin in order to form a polymer layer which inhibits blister formation;[7] which inhibits irritation arising from prosthetic devices;[8] which inhibits skin irritation and infection due to incontinence;[9] which can be used as a surgical drape;[10] and the like. The liquid character of these compositions assist in application onto the skin and in the formation of a thin unbroken polymer film on the skin.

It is well known, however, that lower alkyl cyanoacrylate esters do not form a flexible polymer film on mammalian skin but, rather, a brittle polymer film is formed which lacks long term integrity due to cracking, etc. Accordingly, compositions comprising lower alkyl cyanoacrylate esters are typically formulated to comprise a compatible plasticizer which imparts flexibility to the polymer film such that the integrity of the polymer coating is not compromised.[11] Suitable plasticizers heretofore disclosed in the art for use in such cyanoacrylate compositions include dioctyl phthlate, acetyl tri-n-butyl citrate, and the like.[11]

The use of plasticizers in such compositions poses problems such as compatibility of the plasticizer with the composition and compatibility of the plasticizer with mammalian skin.[11] In fact, incomplete compatibility of the plasticizer with mammalian skin as measured by skin irritation is often balanced by the need to impart flexibility to the polymer film and plasticizers are often selected based on there ability to impart only minimal skin irritation.

Notwithstanding issues arising from the compatibility of the plasticizer in a cyanoacrylate composition, any plasticizer used in such cyanoacrylate compositions acts as a diluent which results in weakening of the adhesion of the resulting polymer film to the skin. Moreover, the plasticizer is not incorporated into the polymer backbone but, rather, is integrated into the polymer film and there is a maximum amount of plasticizer which can be added to the cyanoacrylate composition while still allowing the composition to form such a polymer film on the skin. In this regard, small molecule plasticizers can be leached out of the polymeric film.

As is apparent, the incorporation of a plasticizer into the cyanoacrylate composition often comprises balancing the benefits versus the detriments arising from the use of the plasticizer. Contrarily, cyanoacrylate compositions which result in the formation of a flexible cyanoacrylate polymer film on mammalian skin without the use of a conventional plasticizer would be particularly desireable since the detrimental aspects arising from incorporation of the plasticizer would be obviated. Preferably, for ease of delivery, the composition comprising the $C_1$ to $C_8$ alkyl cyanoacrylate ester should be a liquid.

SUMMARY OF THE INVENTION

This invention is directed to novel cyanoacrylate compositions comprising lower alkyl cyanoacrylate esters suitable for topical application to human skin. In particular, this invention is directed, in part, to the discovery that the addition of a $C_{10}$–$C_{12}$ alkyl cyanoacrylate ester to a $C_1$ to $C_8$ alkyl cyanoacrylate ester provides for a composition which forms a flexible cyanoacrylate polymer on mammalian skin without the need to add a plasticizer.

Because the $C_{10}$–$C_{12}$ alkyl cyanoacrylate ester contains a reactive vinyl group, this ester is incorporated into the polymer backbone and becomes an integral part of the polymeric film formed on the mammalian skin. Accordingly, there is no little or no loss of adhesion to the skin by incorporation of this component into the cyanoacrylate composition. Moreover, it is contemplated that the composition will have improved skin compatibility as compared to prior art compositions comprising a conventional plasticizer.

The amount of $C_{10}$–$C_{12}$ alkyl cyanoacrylate ester added to the $C_1$ to $C_8$ alkyl cyanoacrylate is an amount sufficient to provide enhanced flexibility to the polymeric film. Enhanced flexibility is achieved by comparison to the film formed by only by the $C_1$ to $C_8$ alkyl cyanoacrylate ester while maintaining the liquid characteristic of the composition at room temperature.

Accordingly, in one of its composition aspects, this invention is directed to a $C_1$ to $C_8$ alkyl cyanoacrylate ester composition which comprises (a) a reactive $C_1$ to $C_8$ cyanoacrylate ester monomer or reactive oligomer which, in monomeric form, is represented by the formula:

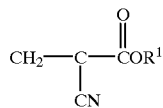

wherein $R^1$ is a $C_1$ to $C_8$ alkyl group; and (b) a sufficient amount of a $C_{10}$–$C_{12}$ cyanoacrylate monomer or reactive oligomer to provide enhanced flexibity to the polymeric film formed on mammalian skin as compared to the polymeric film formed from said $C_1$ to $C_8$ alkyl cyanoacrylate ester while maintaining the liquid characteristic of the composition at room temperature wherein, in monomeric form, the $C_{10}$–$C_{12}$ cyanoacrylate is represented by the formula:

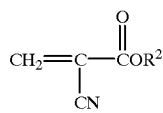

wherein $R^2$ is decyl, undecyl, dodecyl or mixtures thereof. Branched or straight chain isomers of decyl, undecyl and dodecyl can be used but preferably the isomer is straight chain, i.e., n-decyl, n-undecyl and n-dodecyl.

In a preferred embodiment, the composition comprises from about 20 to about 80 weight percent of $C_1$ to $C_8$ alkyl cyanoacrylate ester and from about 80 to about 20 weight percent of the $C_{10}$–$C_{12}$ alkyl cyanoacrylate ester based on the total weight of the composition.

In another preferred embodiment, the composition does not comprise any plasticizer.

In another preferred embodiment, the composition described above further comprises an antimicrobially effective amount of a compatible antimicrobial agent. Preferably, compositions preferably comprise from about 1 to about 30 and more preferably 3 to 20 weight percent of the compatible antimicrobial agent either as a solution or as a suspension based on the total weight of the composition.

In still another preferred embodiment, the cyanoacrylate composition comprises an effective amount of a polymerization inhibitor. Suitable polymerization inhibitors include, by way of example, sulfur dioxide, glacial acetic acid, hydroquinone and hindered phenols (e.g., 4-methoxyphenol), and the like.

In one preferred embodiment, the cyanoacrylate composition of this invention is sterilized by use of E-beam sterilization as disclosed in UK Patent Application Serial No. 9820457.1, filed Sep. 18, 1998 which application is incorporated herein by reference in its entirety. When so sterilized, the polymerization inhibitor comprises a mixture of a biocompatible acid polymerization inhibitor and a biocompatible free radical polymerization inhibitor to inhibit polymerization of the cyanoacrylate ester. The preferred mixture of polymerization inhibitors is a biocompatible acid polymerization inhibitor such as sulfur dioxide, glacial acid acid and other well known acid polymerization inhibitors and a biocompatible free radical polymerization inhibitor including hydroquinone and hindered phenols (e.g., 4-methoxyphenol). The acid polymerization inhibitor is preferably $SO_2$ which is preferably employed at from about 50 to 1000 ppm, more preferably from about 50 to 500 ppm, and even more preferably from about 200 to 500 ppm, based on the total weight of the composition. The free radical inhibitor is preferably hydroquinone which is preferably employed at a concentration of from about 50 to 250 ppm and more preferably at about 150 ppm. In a particularly preferred embodiment, the polymerization inhibitor is selected such that it does not form decomposition products on exposure to E-beams which are toxic or irritating to mammalian skin or which cause premature polymerization or prevent the polymerization of the cyanoacrylate ester composition.

Sterilization, when desired, can be achieved by adding the cyanoacrylate ester composition of this invention to a packaging element and exposing the packaging element to a sufficient dosage of E-beam irradiation maintained at an initial fluence of at least 2 $\mu$Curie/cm$^2$ to sterilize both the packaging element and the cyanoacrylate ester composition therein without gelling the composition wherein the average bulk density of the materials comprising the packaging element is less than about 0.2 gm/cm$^3$.

In one of its method aspects, this invention is directed to a method for enhancing the flexibility of a polymeric film formed on mammalian skin by polymerization on said skin of a $C_1$ to $C_8$ alkyl cyanoacrylate ester composition free of added plasticizer which method comprises adding to the $C_1$ to $C_8$ alkyl cyanoacrylate ester composition a sufficient amount of a polymerizable $C_{10}$–$C_{12}$ alkyl cyanoacrylate ester monomer or reactive oligomer to provide enhanced flexibity to the polymeric film.

DETAILED DESCRIPTION OF THE PREFERRED EMBODIMENTS

As above, this invention is directed to mixed alkyl cyanoacrylate compositions. However, prior to describing this invention in further detail, the following terms will first be defined.

Definitions

As used herein, the following terms have the following meanings:

The term "$C_1$ to $C_8$ alkyl cyanoacrylate ester compositions" or "$C_1$ to $C_8$ cyanoacrylate compositions" refers to polymerizable formulations comprising polymerizable cyanoacrylate ester monomers and/or oligomers which, in their monomeric form, are preferably compounds represented by the formula:

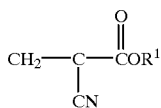

wherein $R^1$ is an alkyl group of from 1 to 8 carbon atoms. Particularly preferred $C_1$ to $C_8$ alkyl cyanoacrylate esters include n-butyl and n-octyl cyanoacrylate esters represented by the formula:

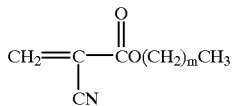

where m is an integer equal to either 3 (n-butyl) or 7 (n-octyl).

$C_{10}$–$C_{12}$ alkyl cyanoacrylate esters refer to a polymerizable monomer or reactive oligomer which, in monomeric form, represented by the formula:

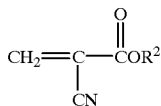

wherein $R^2$ is decyl, undecyl, dodecyl or mixtures thereof.

Polymerizable alkyl cyanoacrylate esters are known in the art and are described in, for example, U.S. Pat. Nos. 3,527,224; 3,591,676; 3,667,472; 3,995,641; 4,035,334; and 4,650,826[1-6], the disclosures of each are incorporated herein by reference in their entirety.

The polymerizable alkyl cyanoacrylate ester compositions described herein rapidly polymerize in the presence of water vapor or tissue protein, and these prepolymers bond human skin tissue without causing histotoxicity or cytotoxicity.

Such polymerizable cyanoacrylate esters are sometimes referred to herein as prepolymers and compositions comprising such esters are sometimes referred to herein as prepolymer compositions.

The term "a biocompatible polymer" refers to polymers which, as iodine complexes (adducts), are compatible with in vivo applications of cyanoacrylate ester compositions onto mammalian skin including human skin. Representative polymers include polyvinylpyrrolidone, copolymers comprising polyvinylpyrrolidone which are optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodide anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents. Surprising, it has been found that iodine/polymer complexes are compatible in cyanoacrylate compositions. In fact, elemental (solid) iodine is incompatible with cyanoacrylate compositions because the addition of elemental iodine renders such compositions non-polymerizable on mammalian skin. Accordingly, complexation of the iodine with the biocompatible polymer is apparently essential for compatibility with the cyanoacrylate composition.

A preferred iodine/polymer complex for use in the compositions of this invention is a polyvinylpyrrolidone iodine complex which is described in, for example, the Tenth Edition of the Merck Index, Published by Merck & Co., Rahway, N.J., USA (1983). This complex is commercially available under the name "povidone-iodine" from BASF, Mt. Olive, N.J., USA.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. Other biocompatible plactizers include low molecular weight acrylic copolymers. The particular biocompatible plasticizer employed is not critical and preferred plasticizers include dioctylphthalate and acetyl tri-n-butyl citrate.

The term "polymerization inhibitor" refers to conventional acid polymerization inhibitors and free radical inhibitors of cyanoacrylate esters including materials such as acid polymerization inhibitors including sulfur dioxide, glacial acetic acid, and the like and free radical polymerization inhibitors such as hydroquinone, 4-methoxyphenol and the like.

Because of its compatibility with topical skin applications, the acid polymerization inhibitor is preferably sulfur dioxide which is preferably employed at from about 50 to 1000 ppm, more preferably from about 50 to 500 ppm and even more preferably 200 to 500 ppm, based on the total weight of the composition. Other preferred acid polymerization inhibitors include glacial acetic acid and other organic acids (e.g., $C_2$ to $C_6$ organic acids).

Preferred free radical inhibitors include hydroquinone which is preferably employed at from about 50 to 250 ppm. Other free radical inhibitors include hydroquinone monomethyl ether, hindered phenols such as 4-methoxyphenol, 2,6-di-tert-butylphenol, and the like.

Mixtures of free radical polymerization inhibitors and acid polymerization inhibitors are often used.

The term "antimicrobial agent" refers to agents which destroy microbes (i.e., bacteria, fungi, viruses and microbial spores) thereby preventing their development and pathogenic action.

Compositions

The cyanoacrylate esters compositions used in the methods of this invention are prepared by conventional techniques of mixing the appropriate components until homogenous. Specifically, the requisite amounts of the polymerizable $C_1$ to $C_8$ alkyl cyanoacrylate ester monomer or reactive oligomer are combined with the polymerizable $C_{10}$–$C_{12}$ alkyl cyanoacrylate ester monomer or reactive oligomer and the resulting composition is mixed until homogenous.

In general, a sufficient amount of a $C_{10}$–$C_{12}$ alkyl cyanoacrylate ester monomer or reactive oligomer is added to the $C_1$ to $C_8$ alkyl cyanoacrylate ester to provide enhanced flexibility to the polymeric film formed on mammalian skin as compared to the polymeric film formed from the $C_1$ to $C_8$ alkyl cyanoacrylate ester alone while maintaining the liquid characteristic of the composition at room temperature. If necessary, gentle heating may be employed to facilitate formation of the liquid composition.

As shown in the example below, the addition of at least about 10 weight percent of $C_{10}$–$C_{12}$ alkyl cyanoacrylate ester monomer or reactive oligomer to the $C_1$ to $C_8$ alkyl cyanoacrylate ester substantially increases the flexibility of the polymer film formed therefrom as compared to the flexibility of the film formed from the $C_1$ to $C_8$ alkyl cyanoacrylate ester alone. Additionally, 100% $C_{10}$–$C_{12}$ alkyl cyanoacrylate ester is a solid at room temperature and, accordingly, would not provide the requisite liquid characteristic for storing and applying the composition. In view of the above, the composition of this invention preferably comprises from about 10 to about 80 weight percent of the $C_1$ to $C_8$ alkyl cyanoacrylate ester and from about 90 to about 20 weight percent of the $C_{10}$–$C_{12}$ alkyl cyanoacrylate ester based on the total weight of the composition. Even more preferably, the composition of this invention comprises from about 20 to about 80 weight percent of the $C_1$ to $C_8$ alkyl cyanoacrylate ester and from about 80 to about 20 weight percent of the $C_{10}$–$C_{12}$ alkyl cyanoacrylate ester based on the total weight of the composition. In still another preferred embodiment, the the composition of this invention comprises from about 50 to about 90 weight percent of $C_1$ to $C_8$ alkyl cyanoacrylate ester and from about 10 to about 50 weight percent of the $C_{10}$–$C_{12}$ alkyl cyanoacrylate ester based on the total weight of the composition.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate ester employed in these compositions is almost entirely in monomeric form and the composition has a viscosity of from about 5 to about 500 centipoise at 20° C.

A thickening agent is optionally employed to increase the viscosity of the composition, which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239 and 4,038,345 both of which are incorporated herein by reference in their entirety. Thickening agents are deemed to be biocompatible if they are soluble or dispersible in the composition and are compatible with the skin as measured by the lack of moderate to severe skin irritation.

Additionally, the cyanoacrylate compositions described herein preferably include a polymerization inhibitor in an effective amount to inhibit premature polymerization of the composition. Preferred polymerization inhibitors are described above.

The polymerizable cyanoacrylate ester compositions may additionally contain one or more optional additives such as colorants, perfumes, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell. The amount of each of these optional additives employed in the composition is an amount necessary to achieve the desired effect.

In a particularly preferred embodiment, the cyanoacrylate composition further comprises an antimicrobially effective amount of a compatible antimicroial agent. Such compositions preferably comprise from about 1 to about 30 and more preferably 3 to 20 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, the composition preferably comprises from about 1 to about 30 weight percent and more preferably from about 3 to 20 weight percent of povidone-iodine based on the total weight of the composition.

Alkyl cyanoacrylate ester compositions comprising, for example, povidone-iodine are described by Greff, et al., U.S. Pat. No. 5,684,042 which patent is incorporated herein by reference in its entirety. Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone, etc. Preferably, however, the iodine containing polymer is Povidone Iodine which is commercially available from a number of sources.

The use of a compatible antimicrobial agent in the composition permits the agent to be released from the polymeric film formed on mammalian skin thereby inhibiting microbial growth under this film. Additionally, since the film is maintained on mammalian skin for 1–4 days after formation, the release of antimicrobial agent further provides long term anti-infection benefits.

Utility

The compositions of this invention are useful in providing $C_1$ to $C_8$ alkyl cyanoacrylate ester compositions which form a flexible film on mammalian skin without the need to add a plasticizer to the composition. As noted above, these compositions can be used to form a polymer layer on mammalian skin which layer inhibits blister formation;[7] which inhibits irritation arising from prosthetic devices;[8] which inhibits skin irritation and infection due to incontinence;[9] which can be used as a surgical drape[10]; and the like.

EXAMPLES

In the following examples, unless otherwise stated, all temperatures are in degrees Celcius. In addition, the following abbreviations have the following meanings:

CA=cyanoacrylate
cp=centipoise
mm=millimeters
sec=seconds
w/w=weight to weight

Example 1

The purpose of this example is to evaluate the properties of alkyl cyanoacrylate mixtures specifically mixtures comprising n-butyl and n-decyl cyanoacrylates. In this regard, six cyanoacrylate compositions containing different proportions of n-butyl and n-decyl cyanoacrylate monomers were prepared. The formulations were packaged in individual bottles. As a comparison, formulations comprising (i) n-butyl cyanoacrylate, (n-butyl CA) (ii) n-decyl cyanoacrylate (n-decyl CA) and (iii) n-butyl cyanoacrylate and 20% dioctylphthalate (DOP), a conventional plasticizer, were also tested. The odor, viscosity, melting point, flexibility, skin setting time and plate setting time were measured. Measurements were conducted about 25° C. The results are shown in Table 1.

The flexibility test refers to the ability of a 1.2 mm thick polymer film, that is formed upon curing of the particular formulation, to bend without breaking. Specifically, each film was subjected to bending at 45 degree increments. In table 1, "+" denotes that the film did not break when subject to 45 degrees bending but broke at 90 degrees, "++" denotes that the film did not break when subject to 90 degrees bending but broke at 135 degrees, and so forth. The skin and plate setting times refer to the length of time required for one drop of formulation deposited from a 21 gauge syringe needle to cure on the skin of a hand and on a petri dish containing a layer of EARLS balance salt solution, respectively. The polymerization was viewed with a 7X magnifying glass.

TABLE 1

| Wt Ratio of n-butyl to n-decyl | Melting point (°C.) | Flexibility | Odor | Skin setting time (sec) | Plate setting time (sec) | Visosity at 25° C. (cp) |
|---|---|---|---|---|---|---|
| 30:70 | 10° to 12° | ++++ | <mild | 10 | 4–5 | 5.29 |
| 50:50 | 0° to 4° | >++++ | mild | 25 | 20 | 5.21 |
| 60:40 | −10° to −12° | ++++ | mild | 12 | 8 | 4.52 |
| 70:30 | −15° | +++ | mild | 14 | 10 | 4.85 |
| 80:20 | −21° to −24° | +++ | strong | 12 | 14 | 4.11 |
| 90:10 | −32° | + | strong | 10 | 5 | 4.01 |
| n-butyl CA and 20% w/w DOP | −65° | ++ | strong | 6 | 12 | 4.6 |
| n-butyl CA (pure) | −50° to −52° | <+ | very strong | 4 | 5 | 3.1 |
| n-decyl CA (pure) | 22° to 23° | ++++ | <mild | 10–12 | 10 | 7.6 |

As is apparent, polymer films formed from compositions containing at least 10% n-decyl cyanoacrylate demonstrated good flexibility. From the data, it is evident that mixtures containing n-butyl and n-decyl cyanoacrylates wherein the n-butyl cyanoacrylate comprises at least about 20% by weight of the mixture will have a sufficiently low melting point so that the formulation is a liquid at ambient temperatures (e.g., 20° to 25° C.).

Example 2

This example measures the melting point of several cyanoacrylates as well as mixtures of these cyanoacrylates.

| Cyanoacrylate | Melting Point |
|---|---|
| 100% n-butyl CA | −50° to −52°C. |
| 100% n-decyl CA | 22° to 23° C. |
| 30% n-butyl/70% n-decyl CA | 10° to 12° C. |
| 100% n-dodecyl CA | 26° C. |

It is contemplated that the flexibility of polymeric films formed on mammalian skin from other cyanoacrylate esters can likewise be improved by the addition of a effective amount of a $C_{10}$ to $C_{12}$ cyanoacrylate ester. In particular, it is contemplated that the flexibility of polymeric films formed on mammalian skin from cyanoacrylate esters can be improved by the addition of a effective amount of a $C_{10}$ to $C_{12}$ cyanoacrylate ester wherein such cyanoacrylate esters are represented by the formula

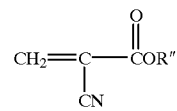

wherein R" is alkenyl of 2 to 10 carbon atoms, cycloalkyl groups of from 5 to 8 carbon atoms, phenyl, 2-ethoxyethyl, 3-methoxybutyl, or a substituent of the formula:

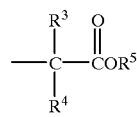

wherein $R^3$ and $R^4$ are independently selected from the group consisting of hydrogen and methyl, and $R^5$ is selected from the group consisting of alkyl of from 1 to 6 carbon atoms, alkenyl of from 2 to 6 carbon atoms, alkynyl of from 2 to 6 carbon atoms, cycloalkyl of from 3 to 8 carbon atoms, aralkyl selected from the group consisting of benzyl, methylbenzyl and phenylethyl, phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

From the foregoing description, various modifications and changes in the composition and method will occur to those skilled in the art. All such modifications coming within the scope of the appended claims are intended to be included therein.

What is claimed is:

1. A $C_1$ to $C_8$ alkyl cyanoacrylate ester composition which comprises:

(a) a reactive $C_1$ to $C_8$ cyanoacrylate ester monomer or reactive oligomer which, in monomeric form, is represented by the formula:

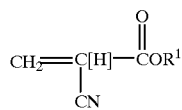

wherein $R^1$ is a $C_1$ to $C_8$ alkyl group; and (b) a sufficient amount of a $C_{10}$–$C_{12}$ alkyl cyanoacrylate ester monomer or reactive oligomer to provide enhance flexibility to the polymeric film formed on mammalian skin as compared to the polymeric film formed from said $C_1$ to $C_8$ alkyl cyanoacrylate ester while maintaining the liquid characteristic of the composition at room temperature wherein, in monomeric form, the $C_{10}$–$C_{12}$ alkyl cyanoacrylate ester is represented by the formula:

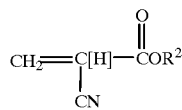

wherein $R^2$ is decyl, undecyl, dodecyl or mixtures thereof.

2. The composition according to claim 1 wherein the $R^2$ decyl, undecyl and dodecyl groups are branched isomers.

3. The composition according to claim 1 wherein the decyl, undecyl and dodecyl groups are straight chain, i.e., n-decyl, n-undecyl and n-dodecyl.

4. The composition according to claim 1 wherein the composition comprises from about 20 to about 80 weight percent of the polymerizable $C_1$ to $C_8$ alkyl cyanoacrylate ester monomer or reactive oligomer and from about 80 to about 20 weight percent of the polymerizable $C_{10}$–$C_{12}$ alkyl cyanoacrylate ester monomer or reactive oligomer.

5. The composition according to claim 1 which is free of plasticizer.

6. The composition according to claim 1 which further comprises an antimicrobially effective amount of a compatible antimicrobial agent.

7. The composition according to claim 1 which further comprises an effective amount of a polymerization inhibitor.

8. The composition according to claim 7 wherein the polymerization inhibitor is selected from the group consisting of sulfur dioxide, glacial acetic acid, hydroquinone, hindered phenols, and mixtures thereof.

9. The composition according to claim 1 wherein the polymerization inhibitor is a mixture of a free radical polymerization inhibitor and an acidic polymerization inhibitor.

10. The composition according to claim 9 wherein the mixture of polymerization inhibitors comprises from about 50 to 1000 ppm of $SO_2$ and from about 50 to 250 ppm of hydroquinone.

11. The composition according to claim 1 wherein in the $C_1$ to $C_8$ alkyl cyanoacrylate ester is selected from the group consisting of n-butyl cyanoacrylate ester and n-octyl cyanoacrylate ester.

12. A method for enhancing the flexibility of a polymeric film formed on mammalian skin by polymerization on said skin of a $C_1$ to $C_8$ alkyl cyanoacrylate ester composition free of added plasticizer which method comprises adding to said $C_1$ to $C_8$ alkyl cyanoacrylate ester composition a sufficient amount of a polymerizable $C_{10}$–$C_{12}$ alkyl cyanoacrylate ester monomer or reactive oligomer to provide enhanced flexibility to the polymeric film formed upon polymerization of the cyanoacrylate composition.

13. The method according to claim 12 wherein the $C_{10}$ to $C_{12}$ alkyl groups are branched isomers.

14. The method according to claim 13 wherein the $C_{10}$ to $C_{12}$ alkyl groups are straight chain, i.e., n-decyl, n-undecyl and n-dodecyl.

15. The method according to claim 12 wherein the composition comprises from about 20 to about 80 weight percent of the polymerizable $C_1$ to $C_8$ alkyl cyanoacrylate ester monomer or reactive oligomer and from about 80 to about 20 weight percent of the polymerizable $C_{10}$–$C_{12}$ alkyl cyanoacrylate ester monomer or reactive oligomer.

16. The method according to claim 12 which is free of plasticizer.

17. The method according to claim 12 which further comprises an antimicrobially effective amount of a compatible antimicrobial agent.

18. The method according to claim 12 which further comprises an effective amount of a polymerization inhibitor.

19. The method according to claim 18 wherein the polymerization inhibitor is selected from the group consisting of sulfur dioxide, glacial acetic acid, hydroquinone, hindered phenols, and mixtures thereof.

20. The method according to claim 12 wherein the polymerization inhibitor is a mixture of a free radical polymerization inhibitor and an acidic polymerization inhibitor.

21. The method according to claim 20 wherein the mixture of polymerization inhibitors comprises from about 50 to 1000 ppm of $SO_2$ and from about 50 to 250 ppm of hydroquinone.

* * * * *